United States Patent [19]

Moriya et al.

[11] Patent Number: 5,196,716

[45] Date of Patent: Mar. 23, 1993

[54] METHOD AND APPARATUS FOR MEASURING INTERNAL DEFECTS FOR POSITION AND DEPTH

[75] Inventors: Kazuo Moriya, Ageo; Hideo Wada; Katsuyuki Hirai, both of Saitama, all of Japan

[73] Assignee: Mitsui Mining & Smelting Co., Ltd., Tokyo, Japan

[21] Appl. No.: 702,087

[22] Filed: May 17, 1991

[30] Foreign Application Priority Data

May 21, 1990 [JP] Japan ................... 2-129182

[51] Int. Cl.$^5$ ............................................. G01N 21/88
[52] U.S. Cl. ..................................... 250/572; 356/239
[58] Field of Search ................. 250/572, 563, 562; 356/430, 431, 240, 239

[56] References Cited

U.S. PATENT DOCUMENTS

| | | | |
|---|---|---|---|
| 3,652,863 | 3/1972 | Gaskell et al. | 250/563 |
| 4,314,763 | 2/1982 | Steigmeier et al. | 356/237 |
| 4,508,450 | 4/1985 | Ohshima et al. | 356/237 |
| 4,725,139 | 2/1988 | Hack et al. | 250/572 |

FOREIGN PATENT DOCUMENTS 0266728 5/1988 European Pat. Off.
0319797 6/1989 European Pat. Off.
119446 5/1987 Japan.

OTHER PUBLICATIONS

Patent Abstracts of Japan, vol. 13, No. 413 (E-820) [3761] Sep. 12, 1989 & JP-A-1 151 243 Mitsui Mining & Smelting Co.

*Primary Examiner*—David C. Nelms
*Assistant Examiner*—T. Davenport
*Attorney, Agent, or Firm*—Bucknam and Archer

[57] ABSTRACT

A method for measuring internal defects of a specimen, comprising the steps of allowing a finely focused laser beam to be incident into a specimen from its surface and observing the scattered light of the said laser beam from inside the said specimen from the surface of the specimen and in a different direction to the optical axis of incidence of the laser beam.

16 Claims, 14 Drawing Sheets $n = 3.4$
$\Theta_v = 12\sim17°$

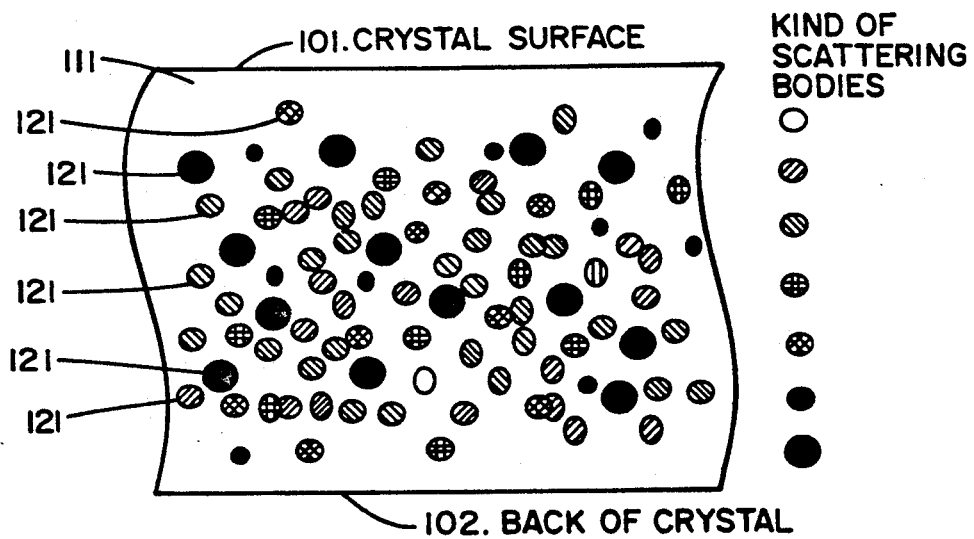
FIG.12a SCATTERING LIGHT IMAGE
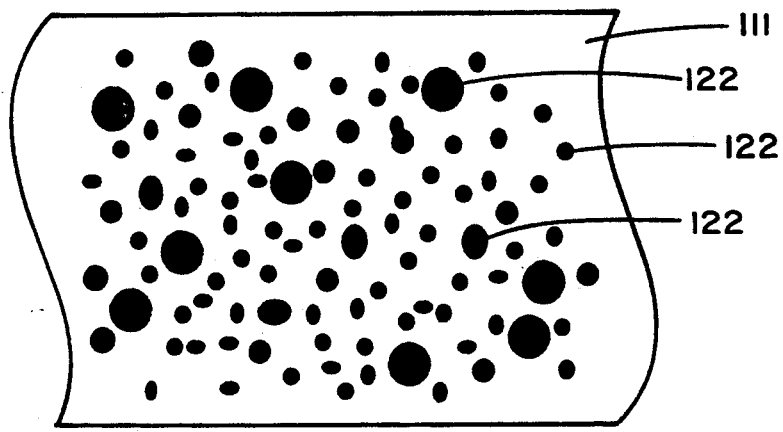
FIG.12b DIGITIZATION PROCESSING
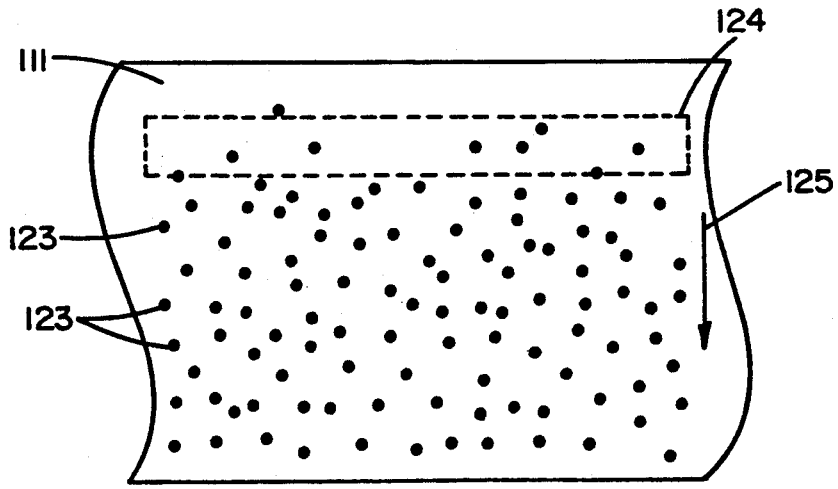
FIG.12c SHRINKING PROCESSING

METHOD AND APPARATUS FOR MEASURING INTERNAL DEFECTS FOR POSITION AND DEPTH

BACKGROUND OF THE INVENTION

1. Field of the Invention

This invention relates to a method and apparatus for measuring internal defects, particularly to a method and apparatus which can measure internal defects of a specimen by allowing a laser beam to be incident into a specimen from its surface and then observing the scattered light of the laser beam from inside the specimen from a different direction to the optical axis of incidence of the laser beam on the surface side of the specimen.

2. Description of the Prior Art

Method and apparatus for measuring internal defects by irradiating a laser beam or the like into an object to be inspected, acquiring its scattered light to obtain data on internal defects of the object and visualizing the defects has been known.

FIG. 16 is a sectional view showing a schematic structure of an internal defect measuring apparatus of this kind. The apparatus shown in the drawing irradiates a laser beam into the object to be inspected, measures the scattered light from a direction substantially orthogonal to the laser irradiating direction and hence visualizes the defects inside the object. This equipment has been disclosed in Japanese Patent Laid-Open No. 151243/1989.

In the apparatus shown in the drawing, a laser beam within the wavelength range of infrared rays (e.g. about 1 μm) is allowed to be incident into a specimen (crystal) 191, such as a silicon wafer, from its side surface 192 as indicated by an arrow 194. The laser beam 194 is scattered by the defects 193 inside the specimen 191. The outcoming scattered light from the specimen 191 as indicated by arrows 195, is detected and magnified by a microscope 196 that is fixed at right angles to the direction of the laser beam 194. The detected and magnified image is converted to an electric signal by a TV camera 197. In this manner the internal defects of the specimen 191 are detected and visualized.

Incidentally, the defects 193 inside the object 191 are depicted on a relatively large scale for the purpose of description in FIG. 16, however, the defects to be detected by internal defect measuring apparatus of this kind are actually very small defects of approx. 20–50 μm in diameter. This also holds true of the defects shown in later drawings.

In the internal defect measuring method or apparatus described above, however, the apparatus is generally in a 90° scattering arrangement such that the direction of the incident laser beam is at 90° to the observation direction of the scattered light as shown in FIG. 16. This is because this arrangement is the one which minimizes distortion of the image and stray light during observation.

In accordance with the conventional system for measuring the internal defects of the object by use of 90° scattering, however, the laser beam is allowed to be incident from the side surface of the object. Therefore, the side surface must be smooth enough that the laser beam can be incident into the object. The side surface of a semiconductor wafer (side surface 192 in FIG. 16), for example, is not generally flat and it is not possible to introduce the laser beam to the inside from the side surface in accordance with the internal defect measuring method (apparatus) shown in FIG. 16. It is therefore necessary to cut or cleave the side surface and to polish it. There is thus the drawback that the specimen must be destroyed in some cases.

Even when defects near the center of a flat sheet-like object such as a semiconductor wafer are measured, the measurement portion must be cut and in this sense, the specimen must be partially destroyed, as well.

SUMMARY OF THE INVENTION

In view of the problems in the prior art technique described above, the present invention is directed to provide a method and apparatus for measuring internal defects which can detect and measure defects in arbitrary positions inside a specimen without destroying the specimen.

In the method and apparatus for measuring internal defects in accordance with the present invention, a finely contracted laser beam is allowed to be incident into the specimen from its surface and the scattered light of the laser beam from inside the specimen is observed from the surface side of the specimen and from a different direction to the direction of the optical axis of incidence of the incident laser beam.

This observation of the scattered light is preferably made from a direction such that the reflected light of the laser beam on the surface of the specimen do not coincide.

Furthermore, it is preferable to employ a structure wherein the wavelength of the laser beam or the temperature of the specimen can be changed so that the depth of incidence of the laser beam from the surface of the specimen can be changed. Particularly when the specimen is a semiconductor material such as silicon (Si) or gallium arsenide (GaAs), the depth of incidence of the laser beam from the surface of the specimen can be easily adjusted by selecting a suitable laser beam wavelength corresponding to the energy gap of the semiconductor material specimen.

Furthermore, the image of the section scanned by the laser beam can be obtained by causing the laser beam to scan inside the specimen.

Scanning of the laser beam inside the specimen may be effected by fixing the specimen and moving the laser beam incident into the specimen or by fixing the laser beam and moving the specimen.

In accordance with the construction of the present invention described above, the laser beam is allowed to be incident from the surface of the specimen. The scattered beams of the laser beam from inside the specimen are observed from the surface side of the specimen but from a different direction to the optical axis of incidence of the incident laser beam. Since the laser beam is incident from the surface of the specimen near the desired measurement position, the side surface of the specimen need not be destroyed in any way. In other words, the defects inside the specimen can be measured non-destructively.

Observation of the scattered light from inside the specimen is preferably made from a direction in which the reflected light of the laser beam on the surface of the specimen is not incident. In this manner the scattered light, having a low intensity, can be detected without interference from the reflected light of the laser beam (or in other words, without superposition with the reflected light).

The depth of incidence of the laser beam from the surface of the specimen can be changed by altering the wavelength of the laser beam or the temperature of the specimen. Accordingly, the beam which is incident from the surface (upper surface) of the specimen, and is reflected from the back (lower surface), can be attenuated and scattered light having even lower intensity can be detected.

If the laser beam is allowed to scan inside the specimen, the image of the section scanned by the laser beam can be obtained. This can be accomplished by fixing the specimen and moving the incident laser beam, or by fixing the laser beam and moving the specimen.

These and other objects and novel features of the present invention will become more apparent from the following description when taken in conjunction with the accompanying drawings.

BRIEF DESCRIPTION OF THE DRAWINGS

FIG. 12a, b, and c, is a schematic view showing the image of the specimen, an image after binary-coding processing and an image after shrinking processing;

DESCRIPTION OF THE PREFERRED EMBODIMENTS

Hereinafter, preferred embodiments of the present invention will be described with reference to the drawings.

Figure 1:
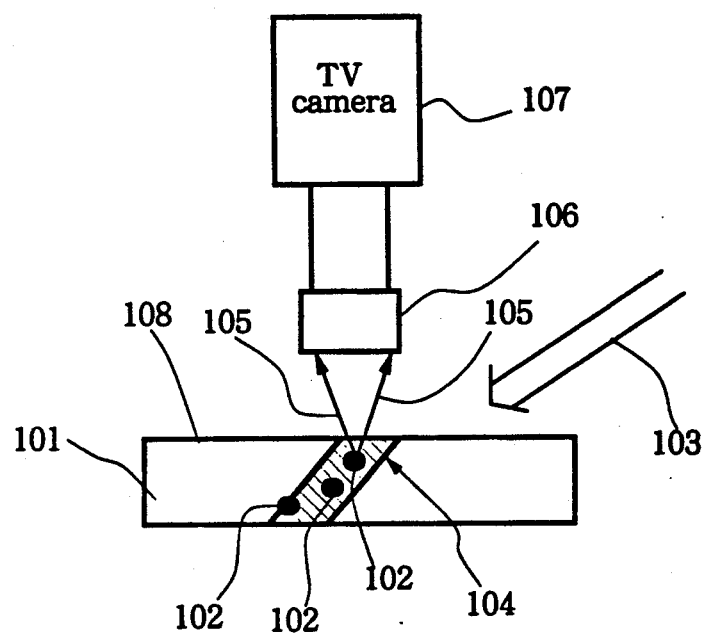
FIG. 1 is a sectional view showing a schematic structure of an internal defect measuring apparatus in accordance with an embodiment of the present invention.

FIG. 1 is a sectional view showing a schematic structure of an internal defect measuring apparatus in accordance with an embodiment of the present invention. The drawing is also a sectional view useful for explaining an internal defect measuring method in accordance with an embodiment of the present invention.

In the drawing, reference numeral 101 represents a crystal as a specimen and reference numeral 102 represents defects inside the specimen 101. The specimen 101 is a sheet-like article and the drawing shows the section cut in the direction of its thickness (the direction perpendicular to the surface of the sheet). Reference numeral 108 represents the surface (top surface) of the specimen 101, and reference numeral 103 is an arrow indicating the direction of incidence of the laser beam into the upper surface 108 of the specimen 101. The hatched portion 104 represents an optical path of the laser beam incident into the specimen 101.

Reference numeral 105 represents arrows which indicate scattered light from the defects 102 existing inside a luminous flux 104 of the laser beam, 106 is a microscope for obtaining a magnified image of the scattered light from these defects 102 and 107 is a TV camera for converting the enlarged image obtained by the microscope 106 to electric signals. The defects are analyzed by later-appearing various methods on the basis of the image signals at of this TV camera 107. The focal length of the microscope 106 is adjustable.

In the apparatus shown in FIG. 1, the laser beam is introduced into the specimen 101 from the upper surface 108 as indicated by the arrow 103. The direction of incidence of the laser beam and the positioning of the microscope 106 are arranged in advance lest the reflected light on the upper surface 108 of the specimen 101 enters into the microscope 106. The laser beam which is introduced into the specimen 101 traverses inside the specimen 101 as shown by the hatched portion 104. If any defects 102 exist inside this luminous flux 104, scattered light are generated by these defects 102. The component (the arrow 105) in the direction of scattered light under the microscope 106 is detected by the microscope 106 to obtain an optically magnified image and this image is taken by the TV camera 107. The defects inside the specimen 101 can be measured on the basis of the electric signals obtained by this method.

Figure 2:
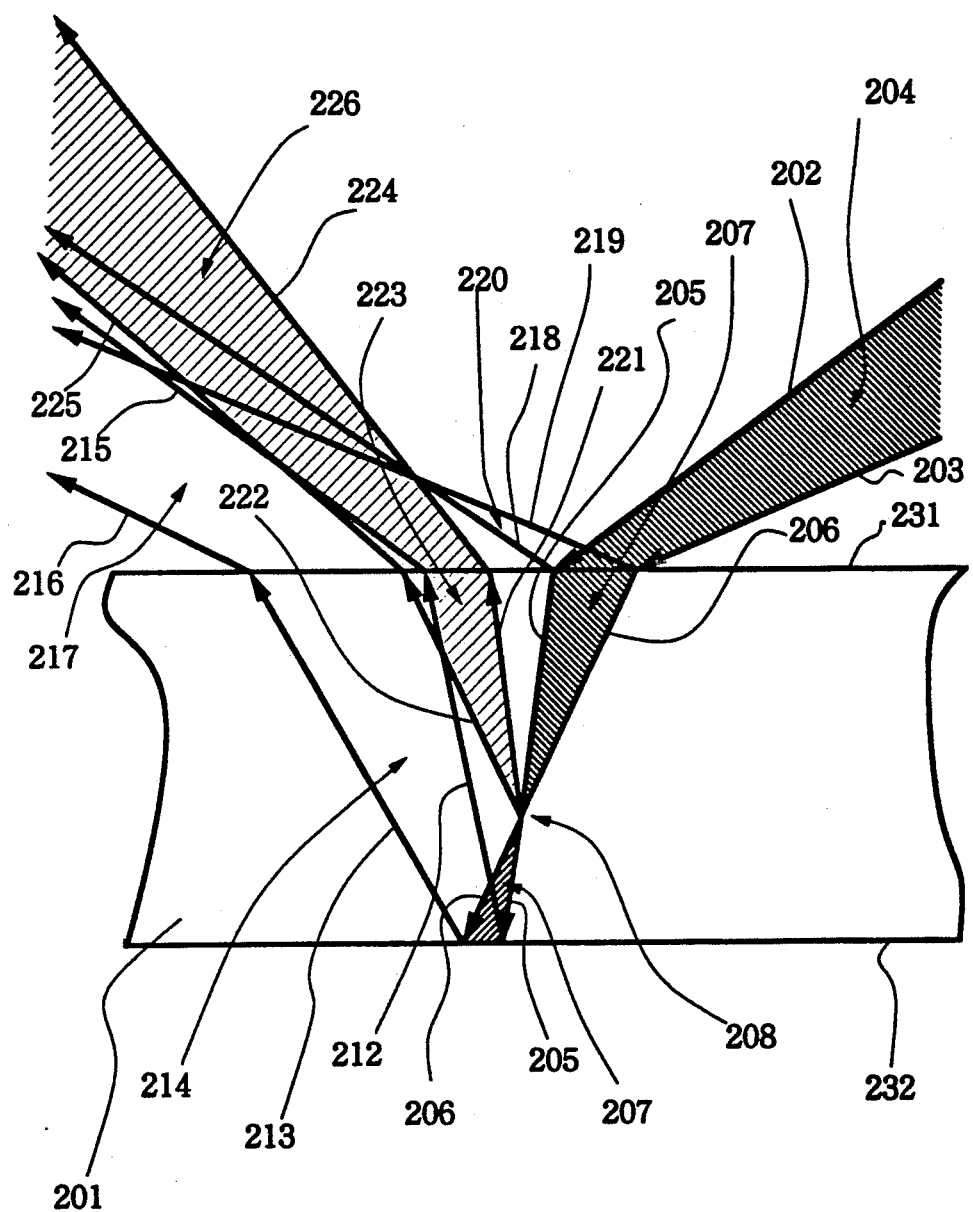
FIG. 2 is a sectional view showing an optical path of a laser beam incident into a specimen.

FIG. 2 is a sectional view showing the optical paths of the laser beam incident into the specimen.

In the drawing, reference numeral 201 represents the section of the specimen, 231 and 232 show the surface (upper surface) and the back (lower surface) of the specimen respectively. The specimen 201 is a plate-like (sheet-like) object and this drawing shows the section when it is cut in the direction of its thickness (the direction perpendicular to the surface of the plate).

The luminous flux of the laser beam as represented by the hatched portion 204 is introduced into the surface 231 of such a specimen 201. Reference numerals 202 and 203 represent the contour lines of the luminous flux 204 of the incident laser beam (or the outermost ray). Here, the case where the laser beam of the type which converge on one point are caused to be incident will be explained.

The luminous flux 204 of the incident laser beam is refracted at the surface 231 of the specimen 201 and travels as the luminous flux 207 defined by the contour lines 205 and 206 inside the specimen 201. This luminous flux 207 converges on one point 208 and reaches further the back 232 of the specimen 201 as a diverging luminous flux.

The luminous flux 207 is reflected on the back 232 of the specimen 201. After being reflected, the luminous flux 207 travels inside the specimen 201 towards its surface 231 as the luminous flux 214 which is defined by the contour lines 212 and 213. The luminous flux 214 which reaches the surface 231 is refracted at this surface 231 and leaves from the surface 231 of the specimen 201 as the luminous flux 217 which is defined by the contour lines 215 and 216.

On the other hand, part of the luminous flux 204 of the incident laser beam is reflected by the surface 231 of the specimen 201 and travels from the surface 231 of the specimen as the luminous flux 220 which is defined by the contour lines 218 and 219.

If any defect exists at the point 208 at which the luminous flux 207 of the incident laser beam converges, scattered light is generated by the defect. The luminous flux 223 which is defined by the contour lines 221 and 222 represents part of components of this scattered light. The luminous flux 232 of this scattered light is refracted by the surface 231 of the specimen 201 and leaves from the surface 231 of the specimen 201 as a luminous flux 226 which is defined by the contour lines 224 and 225.

The luminous flux 226 of this scattered light is detected by the microscope (reference numeral 106 in FIG. 1) so as to measure the defect. The focus of this microscope is adjusted to the position 208. According, image data of one point of the position 208 can be obtained.

In the description given above, it is the scattered light 226 that contains the defect data inside the specimen 201. Therefore, it is preferable to set the direction of incidence of the incident laser beam 204 and the observation direction of the scattered light lest the luminous flux 220 reflected from the surface 231 of the specimen 201 and from its back 232 are incident to the microscope.

Figure 3:
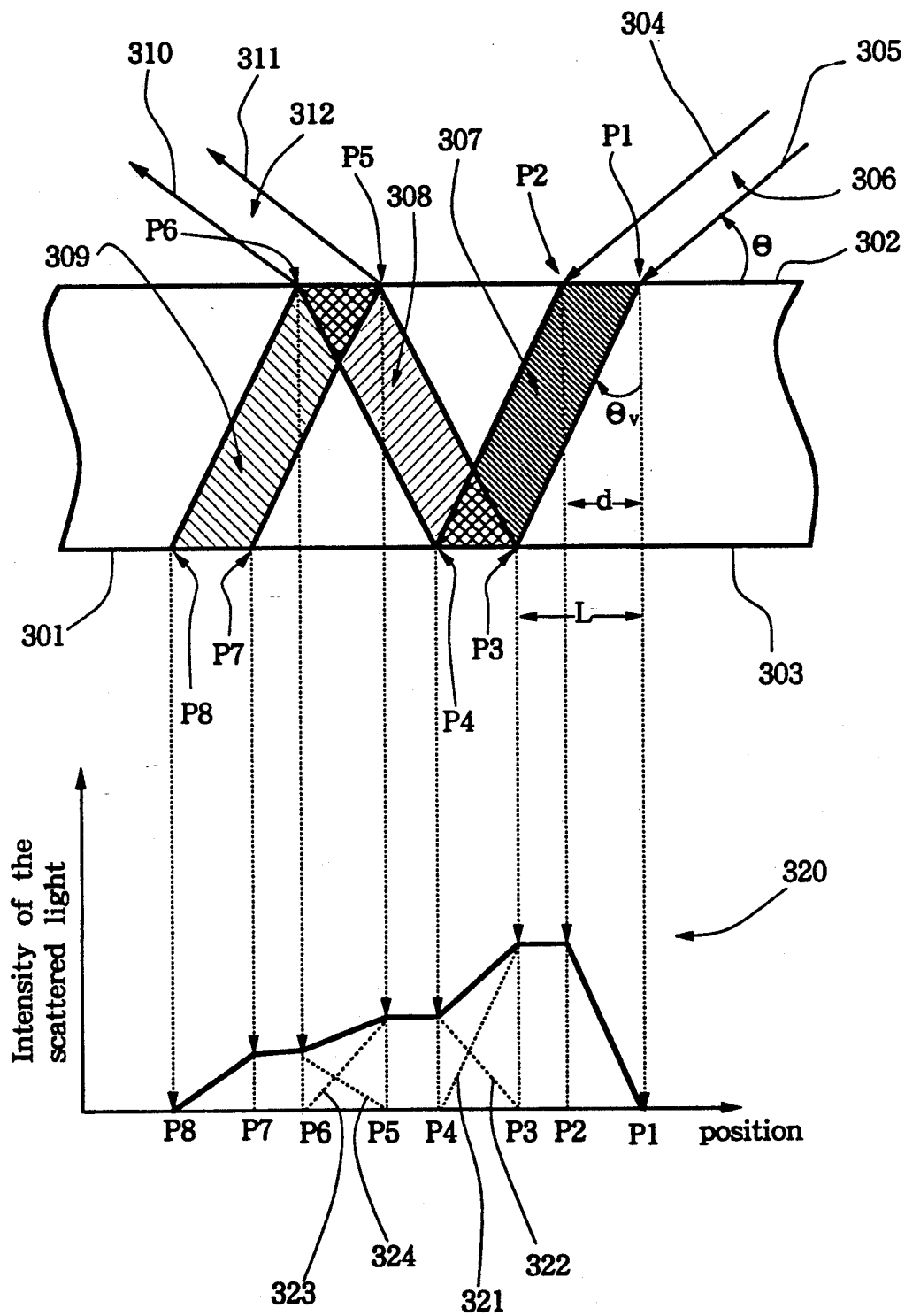
FIG. 3 is a sectional view showing an optical path of a laser beam of a parallel flux of light and is a diagram showing a scattered intensity.

FIG. 3 is a sectional view showing the optical path of the laser beam which is incident into the specimen, similar to that shown in FIG. 2. Whereas the incident laser beam in FIG. 2 is the converging luminous flux that converges to one point, the incident laser beam in FIG. 3 is parallel flux of rays.

In FIG. 3, reference numeral 301 represents the section of the specimen, 302 does the surface (upper surface) of the specimen and 303, the back (lower surface) of the specimen. The specimen 301 is a plate-like object and this drawing shows the section cut in the direction of its thickness (the direction perpendicular to the surface of the plate).

The luminous flux 306 of the laser beam defined by contour lines 304, 305 is allowed to be incident into the surface 302 of such a specimen 301. Symbol $\theta$ represents the angle defined between the surface 302 of the specimen 301 and the incident luminous flux 306. This angle will be hereinafter referred to as the "angle of incidence". The position of the beam, which is incident with the angle of incidence $\theta$ such as one of the contour lines 305 defining the contour of the parallel luminous flux 306, on the surface 302 of the specimen 301 will be called "P1" and the position of the beam such as the contour line 304 on the surface 302 will be called likewise "P2". Furthermore, the distance between these points P1 and P2 will be called "d".

The luminous flux 306 of the incident laser beam is refracted on the surface 302 of the specimen 301, travels as a luminous flux 307 inside the specimen 301 and reaches the back 303 of the specimen 301. The points at which the contour lines of the luminous flux 307 cross the back 303 of the specimen 301 will be called "P3" and "P4", respectively. The distance between the points P1 and P3 will be called "L".

If the back 303 of the specimen 301 is polished, for example, the luminous flux 307 is reflected from this back 303. After it has been reflected, the luminous flux 307 travels as a luminous flux 308 inside the specimen 301 towards the surface 302 and reaches the surface 302. The points at which the contour lines of this luminous flux 308 cross the surface 302 of the specimen 301 will be called "P5" and "P6", respectively, as shown in the drawing. Part of the luminous flux 308 reaching the surface 302 is refracted at this surface 302 and exits as a luminous flux 312 defined by contour lines 310, 311, from the surface 302 of the specimen 301.

Furthermore, part of the luminous flux 308 reaching the surface 302 is reflected by this surface 302, travels as a luminous flux 309 inside the specimen 301 towards the back 303 and reaches the back 303. The points at which the contour lines of this luminous flux 309 cross the back 303 of the specimen 301 will be called "P7" and "P8", respectively, as shown in the drawing.

In this manner the laser beam which is incident into the specimen 301 travels inside the specimen while being reflected by the surface and back inside the specimen.

In the graph 320 shown in a lower part of FIG. 3, the position of the specimen in the transverse direction (the transverse direction of the sheet of drawing) is plotted on the abscissa and the intensity of the scattered light from the position (in the section shown in the drawing) is plotted on the ordinate (the scattered light intensity on the assumption that a defect exists in that position). The intensity of the scattered light at a certain position in the direction of abscissa can be expressed by how much luminous fluxes 307, 308, 309 pass through the segment which is perpendicular to either the surface 302 or back 303 of the specimen 301 through that position. Accordingly, the luminous flux 307 of the incident laser beam increases gradually from the point P1 to P2 and becomes constant between the points P2 and P3.

The scattered light of the luminous flux 307 decreases from the point P3 to the point P4 as indicated by dotted line 321 while the scattered light of the luminous flux 308 increases as indicated by dotted line 322. The intensity of the luminous flux 308 drops slightly due to the reflection on the back 303. Therefore, when the intensity represented by these dotted lines 321 and 322 is added, the total intensity decreases gradually as shown in the drawing. The intensity remains constant from the point P4 to the point P5. The scattered light due to the luminous flux 308 decreases from the point P5 to the point P6 as indicated by dotted line 323 while the scattered light due to the luminous flux 309 increases as represented by dotted line 324. The intensity of the luminous flux 309 drops somewhat due to the reflection on the surface 302. Therefore, when the intensity represented by these dotted lines 323 and 324 is added, the total intensity decreases gradually as shown in the drawing. The intensity remain constant from the point P6 to the point P7 and the scattered light due to the luminous flux 309 decreases gradually from the point P7 to the point P8.

In this manner the laser beam which is incident to the specimen 301 travels inside the specimen while being reflected from the surface and back of the specimen. The defects inside the specimen can be measured by detecting the scattered light of such a laser beam. On the other hand, the scattered light due to the reflected beam inside the specimen can sometimes behave as noise and deteriorate the accuracy of the measurements. Particularly when the back is rapped, the beam reaching the back is scattered and becomes noise. Therefore, it is preferable to adjust the wavelength of the incident laser beam so that only the scattered beam due to the luminous flux 307 shown in FIG. 3 can be detected.

Figure 4:
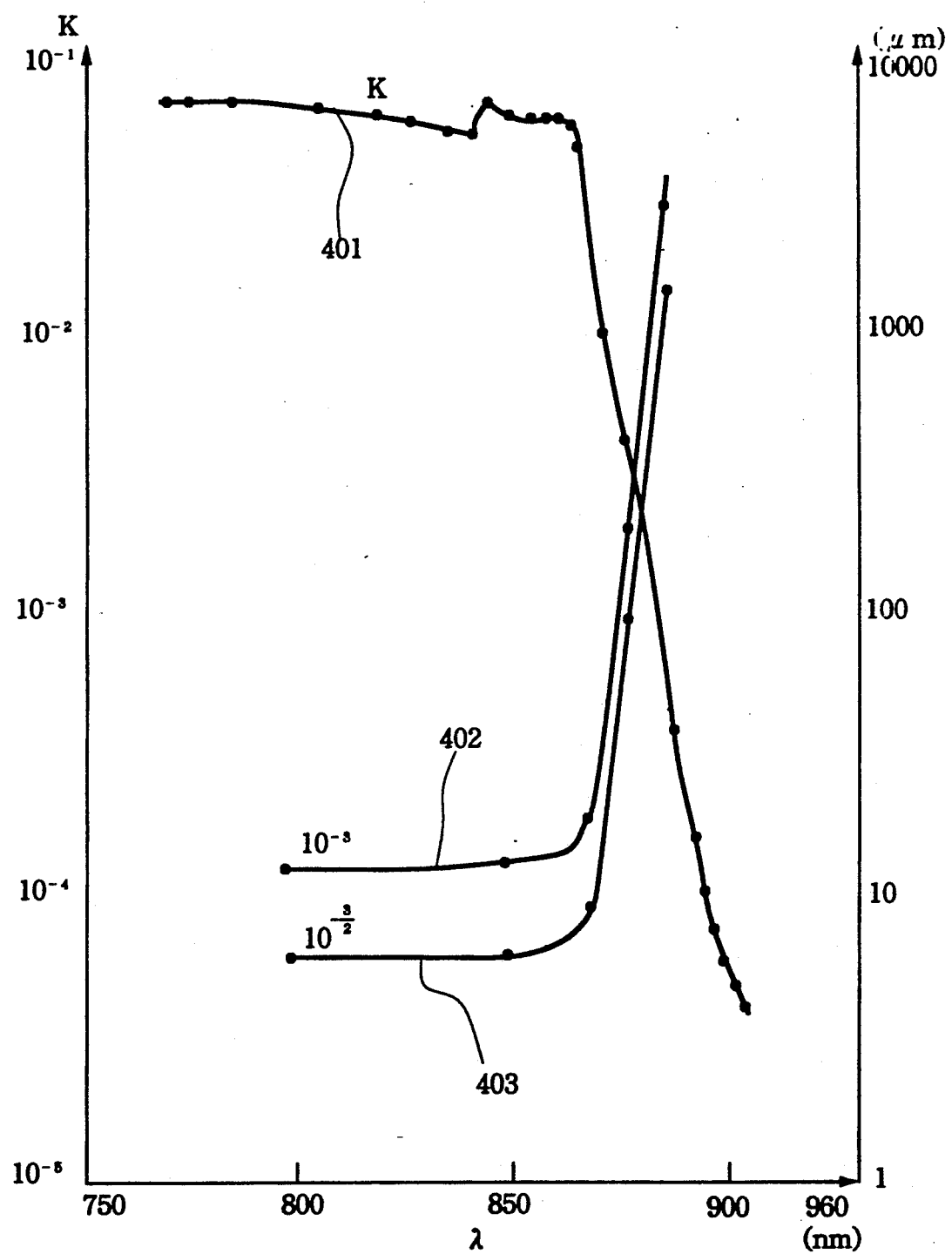
FIG. 4 is a diagram showing an absorption coefficient and attenuation state of GaAs gallium arsenide.

FIG. 4 is a graph showing the absorption coefficient and attenuation state of gallium arsenide (GaAs). Reference numeral 401 represents an absorption coefficient K with respect to the wavelength λ of the laser beam which is allowed to be incident into gallium arsenide. As can be seen from this curve 401, the absorption coefficient K of gallium arsenide decreases sharply from about 870 nm wavelength to 900 nm.

Reference numeral 402 is a curve showing the depth (penetration depth with respect to the attenuation factor of light) from the surface of the specimen at the position, at which the intensity of a laser beam attenuates to $10^{-3/2}$, when the laser beam having a wavelength λ is allowed to be incident into the GaAs specimen. Similarly, reference numeral 403 is a curve showing the depth to the position, at which the intensity of the laser beam attenuates to $10^{-3}$, when the laser beam having the wavelength λ is allowed to be incident into the same specimen.

As can be seen from these curves 402 and 403, when the laser beam having a wavelength λ=850 nm, in this case, is allowed to be incident into GaAs specimen, the intensity of the laser beam attenuates to $10^{-3/2}$ at the depth of about 6.5 μm from the surface and to $10^{-3}$ at the depth of about 10.8 μm. Furthermore, these graphs rise sharply near from the wavelength λ=870 nm. The intensity attenuates to $10^{-3/2}$ near the depth of about 1,500 μm from the surface at the wavelength λ=890 nm and to $10^{-3}$ at the depth of about 3,000 μm from the surface. In this manner, the depth of incidence of the laser beam into the GaAs specimen can be controlled by selecting a suitable wavelength for the incident laser beam.

Due to such characteristics, therefore, when the internal defects of the GaAs specimen are measured, it is for example, possible to attenuate sufficiently the laser beam incident from the surface of the specimen near the back of the specimen by use of the laser beam of a wavelength of about 900 nm. In other words, a luminous flux having sufficient intensity is irradiated onto only the area to be measured by use of only the luminous flux 307 shown in FIG. 3, while the luminous fluxes 308 and 309 can be attenuated sufficiently. Accordingly, it becomes possible to suppress the noise from the scattered light due to the reflected light inside the specimen and to achieve a defect measurement with a higher level of accuracy.

Although the description given above is in the case of a GaAs specimen in particular, the depth of incidence of the laser beam in the crystal can be controlled in various semiconductor materials other than gallium arsenide. This is done by selecting a beam of suitable wavelength depending on the energy gap of the semiconductor material. Since the depth of incidence of the laser beam can be thus controlled, it is possible to suppress the noise due to the internal reflected beam, or the like, and to achieve defect measurement with a higher level of accuracy by irradiating a luminous flux of sufficient intensity onto the area to be measured.

The depth of incidence of the laser beam into the specimen can also be chamged by changing the temperature of the specimen. Therefore, the depth of incidence of the laser beam can be controlled by temperature instead of changing the wavelength of the laser beam as described above.

Figure 5:
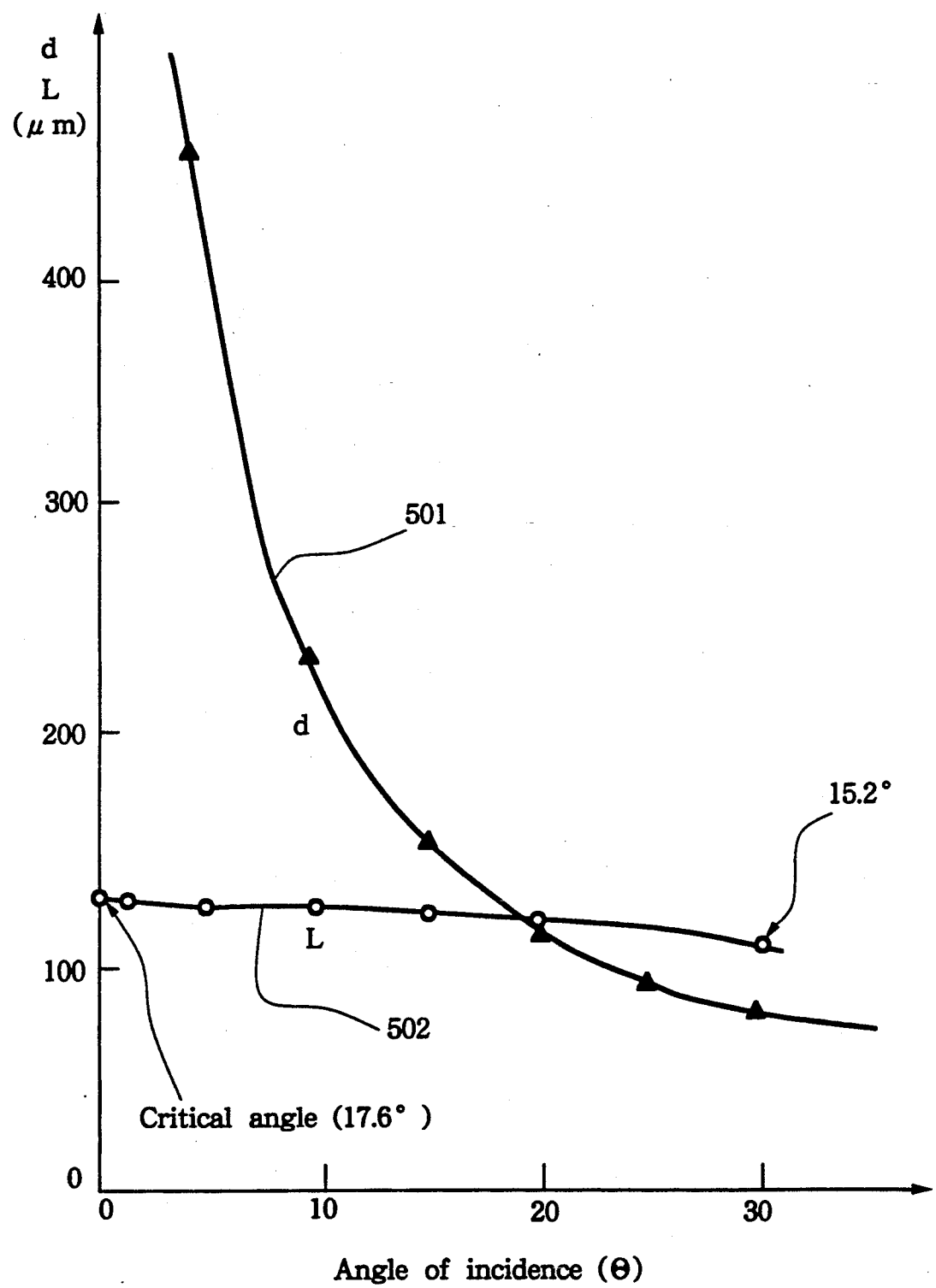
FIG. 5 is a diagram showing the relation between the angle of incidence θ of the laser beam of FIG. 3 and the distance d between P1 and P2, and the relation between the angle and the distance L between P1 and P3.

FIG. 5 is a graph calculated in the case where refrective index is 3.3 and showing the relation between the angle of incidence θ of the laser beam shown in FIG. 3, and the distance d between the points P1 and P2, and the relation between the angle and the distance L between the points P1 and P3. The diameter of the laser beam is several microns. In FIG. 5, reference numeral 501 is a curve showing the value of the distance d with respect to the angle of incidence θ, and reference numeral 502 is a curve showing the value of the distance L with respect to the angle of incidence θ. The angle of incidence θ, or the like, of the position to be measured is determined by taking these curves into consideration.

It can be understood from the graph of FIG. 5 that the distance d changes greatly when the angle of incidence θ is changed, but the distance L does not much change. Furthermore, at θ=0° of the curve 502 (the case where the laser beam is allowed to be incident into the specimen by irradiating it substantially horizontally along the surface of the specimen), $θ_v$ defined in FIG. 3 becomes 17.6° (critical angle) at L=114 μm and $θ_v$=15.2° at θ=30° and L=190 μm. Therefore, it can be understood that this $θ_v$, too, does not much change. As described above, the change of the distance L and angle $θ_v$ with the change of the angle of incidence θ is slow. Accordingly, after the irradiation angle of the laser beam flux is set in such a manner as to irradiate it to the area for to be measured, the laser beam flux can be irradiated substantially to the area of measurement even if the angle of incidence θ is changed. An instrument for observing the scattered light such as a microscope must be disposed in a direction where noise such as the reflected light from the surface of the specimen is not incident into it. Therefore, the angle of incidence θ is often changed in accordance with the measurement condition but this is very preferable because the range in which the change of the angle of incidence θ is permissible is broad.

Figure 6:
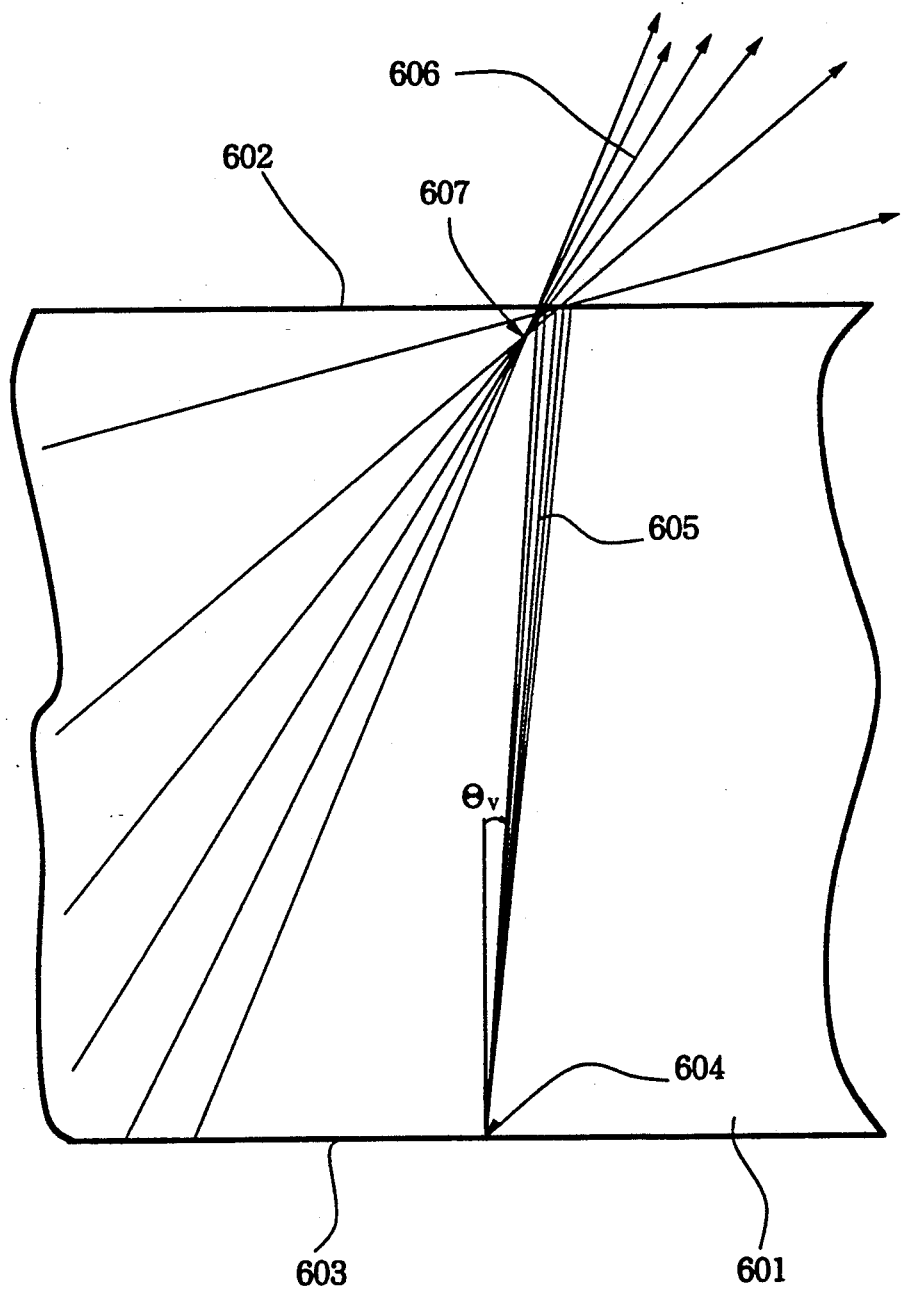
FIGS. 6 to 8 show examples of the optical paths of the laser beam.

FIG. 6 shows the optical path of the scattered light when the laser beam is allowed to be incident into the silicon (Si) specimen having a refractive index of n=3.4. The incident laser beam is omitted. In the drawing, a defect 604 is assumed to exist in a position near the back 603 of the specimen 601 (its section being shown). Among the light scattered by this defect 604, scattered light 605 having an angle $θ_v$ of 12°~17° to the verical direction is refracted at the surface 602 of the specimen 601 and leaves as scattered light 606. Since this scattered light 606 appears as if it were emitted from near the position 607, observation is effected by adjusting the focus of the microscope or the like for observing this scattered light to this position 607.

Figure 7:
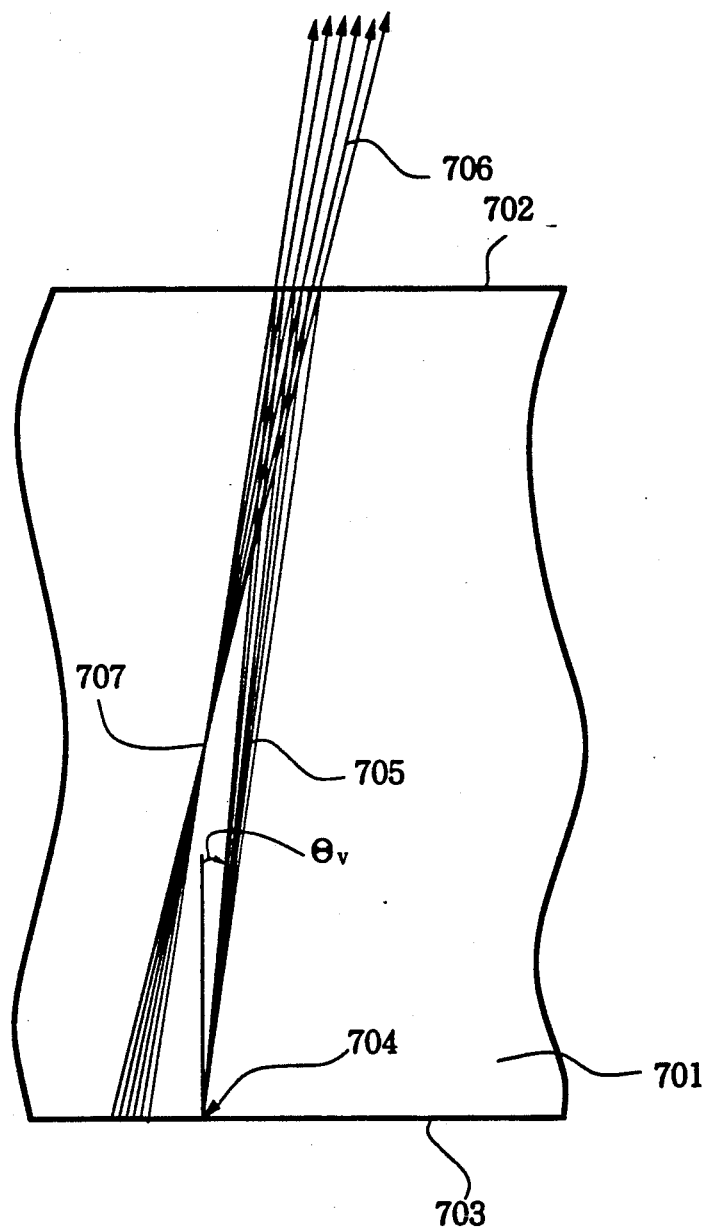

FIG. 7 shows the optical path of the scattered beam when the laser beam is allowed to be incident into a specimen made of glass (or rock crystal) having a refractive index of n=1.6. The incident laser beam is omitted. In the drawing, a defect 704 is assumed to exist in a position near the back 703 of the specimen 701 (whose section is shown). Among the scattered light scattered by this defect 704, scattered light 705 having an angle $θ_v$ of 12°~17° to the perpendicular direction is refracted on the surface 702 of the specimen 701 and leaves as scattered light 706. Since this scattered light 706 appears as if it were emitted from near the position 707, observation is effected by adjusting the focus of the microscope or the like for observing this scattered light to this position 707.

Figure 8:
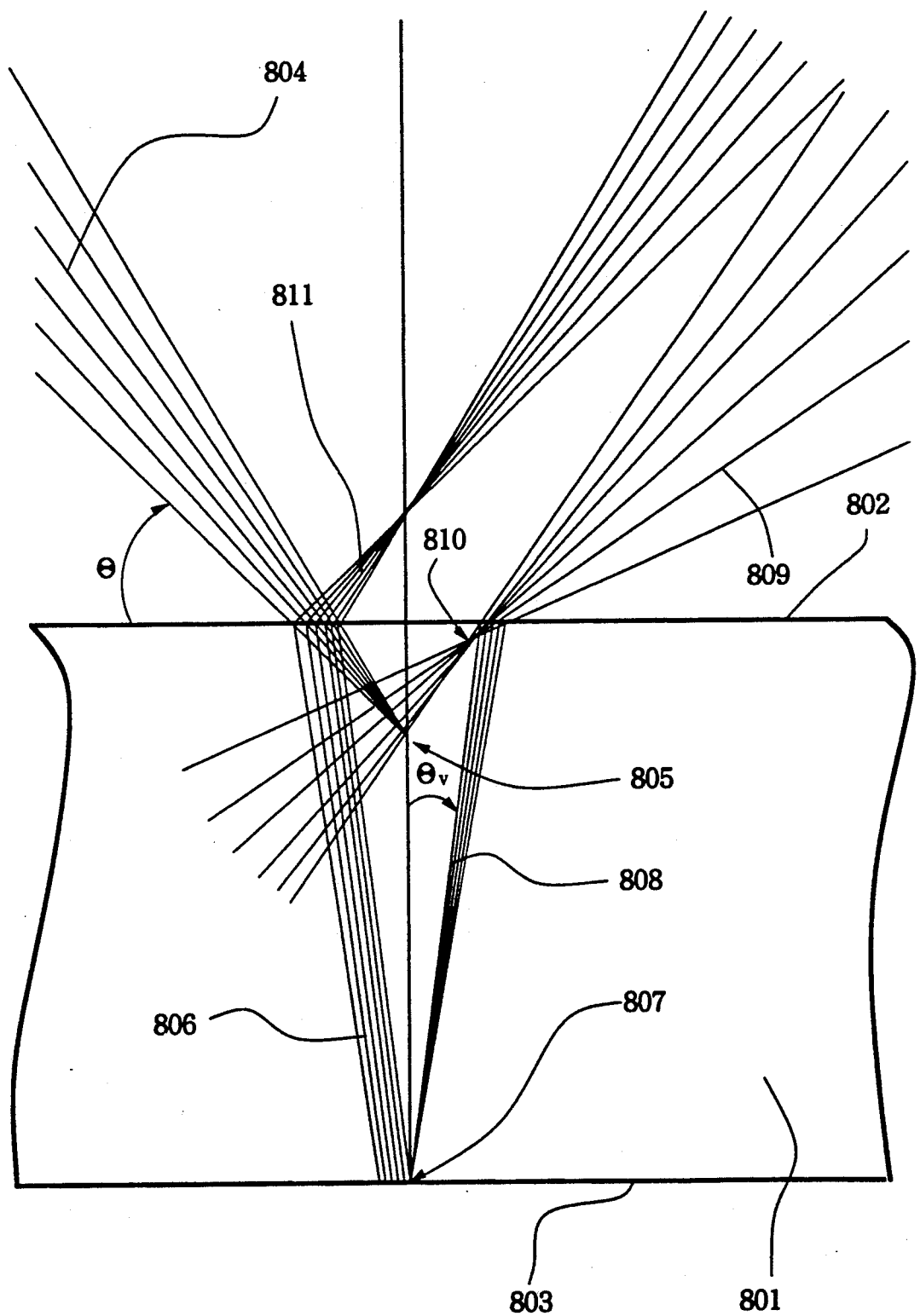

FIG. 8 shows the optical paths when the laser beam is allowed to be introduced with the angle of incidence $\theta = 45° \sim 60°$ into a Si specimen having a refractive index of n=3.4. In the drawing, the incident laser beam 804 is introduced into the specimen 801 (whose section is shown) in such a manner as to converge in a position 805. The angle of incidence $\theta$ of the incident laser beam 804 is within the range of 45° to 60°. The incident laser beam 804 is refracted at the surface 802 of the specimen 801 and travels as a laser beam flux 806. Assuming that a defect 807 exists inside this laser beam flux 806, the scattered light are generated by this defect 807. Among the scattered light generated by this defect 807, the scattered light 808 having an angle $\theta_v$ of $13° \sim 16.5°$ to the perpendicular direction is refracted at the surface 802 of the specimen 801 and outgoes as scattered light 809. Since this scattered light 809 appears as if it were emitted from near a position 810, observation is effected by adjusting the focus of the microscope or the like for observing this scattered light 809 to the position 810.

On the other hand, the incident laser beam 804 is reflected at the surface 802 of the specimen 801 and travels as a reflected laser beam 811. Observation of the scattered beam 809 is effected preferably from such a direction where this reflected laser beam 811 does not enter into the microscope.

Figure 9:
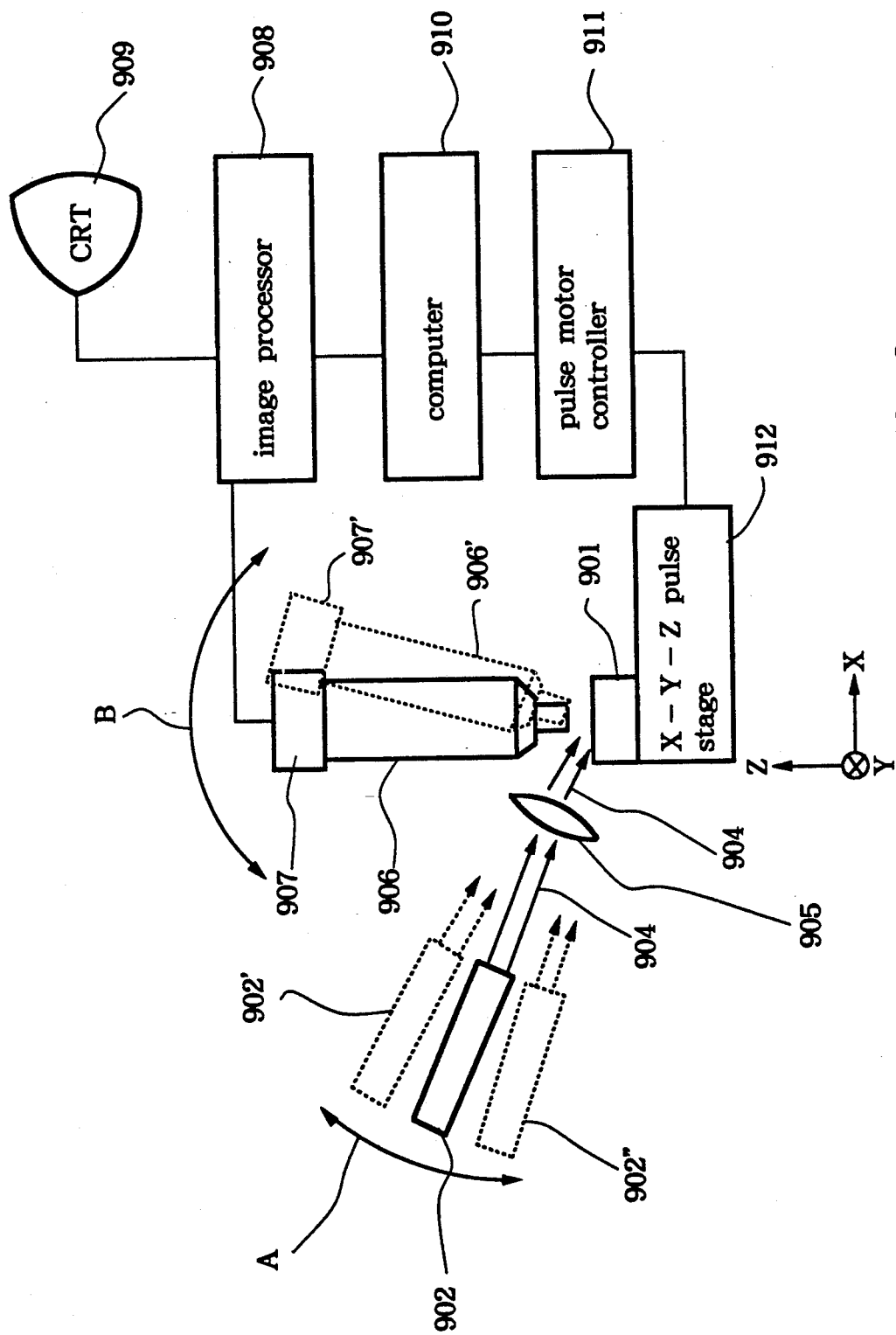
FIG. 9 is a block diagram showing a schematic structure of an internal defect measuring apparatus in accordance with another embodiment of the present invention.

FIG. 9 is a block diagram showing a schematic structure of an internal defect measuring apparatus in accordance with an embodiment of the present invention. In the drawing, reference numeral 901 is a specimen to be measured; 902 is a tunable wavelength laser apparatus for generating a laser beam having a tunable wavelength and being irradiated to the surface of the specimen 901; 904 is arrows indicating the laser beam; and 905 is a lens for converging the laser beam 904. The specimen 901 is a plate-like object, and the drawing shows its section cut in the direction of thickness (direction perpendicular to the surface of the plate).

The tunable wavelength laser 902 changes its position together with a lens 905 and can let the laser beam 904 be incident into the surface of the specimen 901 from an arbitrary direction and at an arbitrary angle of incidence. For example, the tunable wavelength laser 902 moves in the direction indicated by arrow A and can change the angle of incidence of the laser beam 904. Reference numerals 902' and 902" represent example of the positions of the tunable wavelength laser that are moved in this manner.

Reference numeral 906 represents a microscope equipped with an auto-focusing mechanism and 907 is a TV camera for converting the received scattered light into electric signals. The microscope 906 and the TV camera 907 can change their positions so that they can observe the surface of the specimen 901 from an any direction and at an any angle. For instance, the microscope 906 and the TV camera 907 move in the direction represented by arrow B and can change the observation angle of the surface of the specimen 901. Reference numeral 906' and 907' represent example of the microscope 906 and the TV camera 907 after being moved.

Reference numeral 908 represents an image processor for receiving the electric signals from the TV camera 907 and carrying out the image processing. The image processor 908 has a binary-coding function. Reference numeral 909 represents a CRT for outputting as such image data or for displaying and outputting a defect density value obtained as a result of various calculations, and so forth. Reference numeral 910 represents a computer which controls the measurement as a whole, 911 does a pulse motor controller and 912, an X-Y-Z pulse stages which are driven in X-Y-Z directions in accordance with instructions from the pulse motor controller 911. Here, the transverse direction of the sheet of the drawing is the direction of X-axis, the direction perpendicular to the sheet of drawing (from front to back) is the direction of Y-axis and the vertical direction of the sheet of drawing is the direction of Z-axis.

Hereinafter, measurement of very fine defects inside a silicon wafer by this apparatus will be explained.

Figure 10:
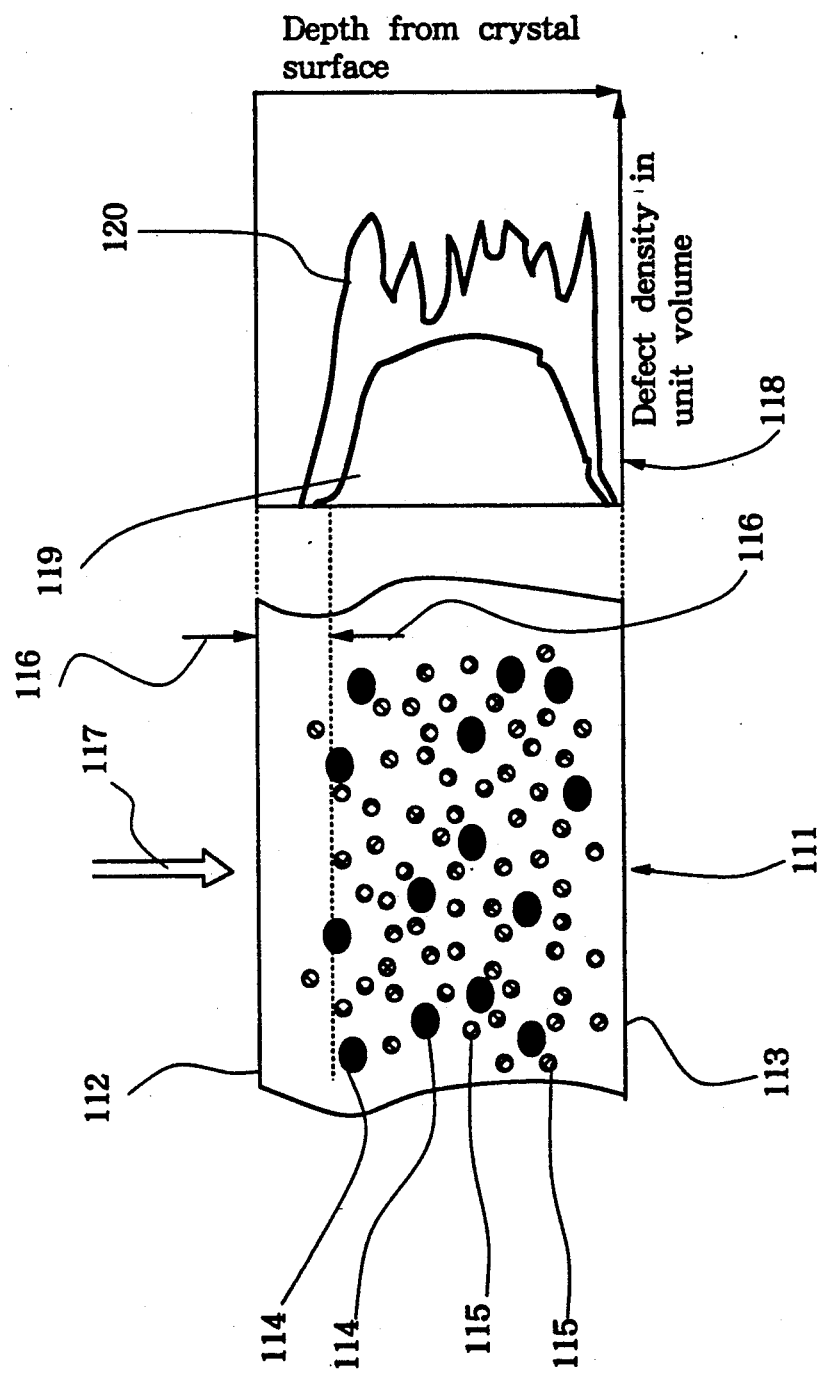
FIG. 10 is a schematic view of a defect image (scattered image) of a specimen and defect density distribution in the direction of depth from the surface.

Measurement of the defect density and DZ (Denuded Zone) width such as shown in FIG. 10 has been carried out for silicon wafers used for fabrication of semiconductor devices. This measurement is carried out using the apparatus shown in FIG. 9 and by image processing the scattered beam obtained as described above.

Reference numeral 111 in FIG. 10 schematically represents the scattered image (image of the specimen by the scattered light) observed by the microscope 906 from a different direction to the optical axis of the incident laser beam on the surface side when a silicon wafer is placed on the pulse stage 912 as the specimen 901 in the apparatus shown in FIG. 9, and the laser beam is allowed to be introduced from the surface of the silicon wafer as indicated by arrow 117. Reference numeral 112 represents the surface of the specimen 111, 113 is the back of the specimen 111, and 114 and 115 are very small defects of various sizes inside the specimen. The distribution of the defects with respect to their depth from the surface of the specimen 111 can be measured as represented by reference numeral 118 on the basis of such a scattered image. Reference numeral 119 represents the distribution of large defects (reference numeral 114) with respect to their depth from the surface 112 of the specimen 111.

Reference numeral 116 represents the width from the surface 112 of the specimen to the position at which the defect density becomes greater than a predetermined value, in other words, a so-called "DZ width". This DZ width was measured in accordance with the following two methods:

1) A method of measurement on the basis of scattered light intensity in the direction of depth from the surface of the specimen.

2) A method of image-processing of the defect density per unit volume with respect to the depth from the surface of the specimen on the basis of the scattered image.

Figure 11:
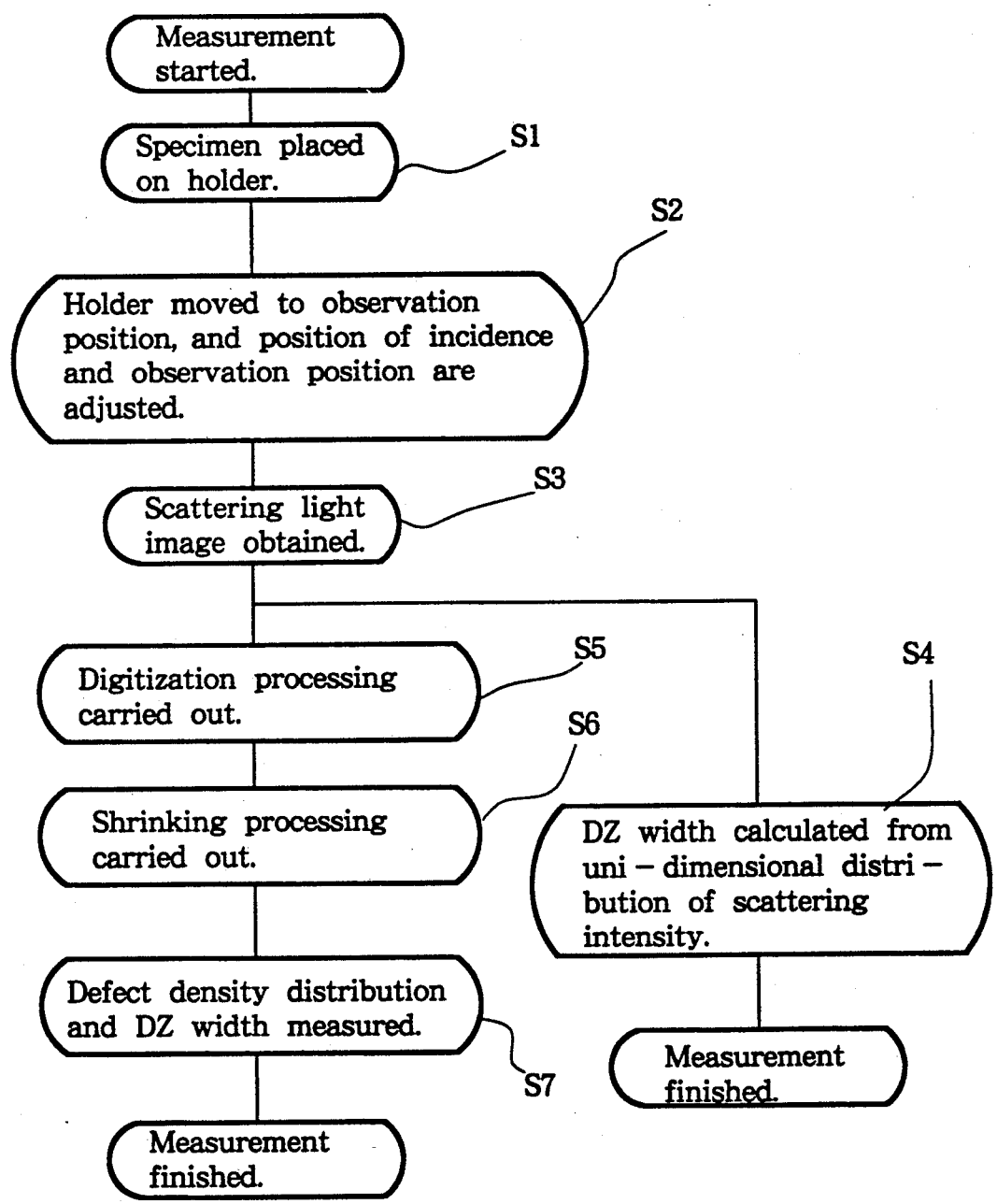
FIG. 11 is a flowchart showing the procedure for DZ width measurement and the defect density distribution.

To begin with, the method (1) of measurement on the basis of the scattered light intensity in the direction of depth from the surface of the specimen will be explained. Steps S1~S4 in FIG. 11 show the procedures of this method (1).

First of all, the specimen 901 is placed on the holder on the X-Y-Z pulse stage 912 in Step S1. Next, the specimen 901 is moved to the observation position in Step S2 and the position of incidence of the laser beam 904 and the observation position of the microscope 906 are adjusted. The position of the microscope 906 is preferably adjusted so that the reflected light of the laser beam 904 from the surface of the specimen 901 does not enter into the microscope 906. The focus of the microscope 906 is adjusted to the converging point of the laser beam inside the specimen 901. The stage 912 is driven to obtain the scattered image in Step S3.

Driving of the stage 912 in Step S3 is carried out in the following manner. The stage 912 is moved in the Y-axis direction while the X and Z coordinates are fixed. At this time the relative positions of the laser beam 904 and the microscope 906 are kept unchanged. (Coincidence of the focus of the microscope 906 and the converging point of the laser beam is kept as such.) The scattered light from the converging point of the laser beam is detected by the microscope 906 during the movement of the stage 912 in the Y-axis direction. In this manner the intensity distribution of the scattered light in the Y-axis direction in the position on the Z-coordinates can be obtained. This operation is also conducted along the section which passes through the X-coordinates of the specimen 901 and is perpendicular to the X-axis. By the operations described above, a scattered image is obtained on the section which is perpendicular to the X-axis (the set of the intensity distributions of the scattered light at each point on the section).

Next, the intensity distribution of the scattered light at several points in the direction of depth (direction of Z-axis) of the specimen is determined from the data of this scattered light in Step S4 and their average is calculated so as to obtain the unidimensional distribution of the scattered light intensity in the Z-axis direction. The DZ width is then determined from this unidimensional distribution. The depth from the surface of the specimen to the position at which the scattered light intensity reaches 30% of the maximum value of the scattered light intensity inside the specimen is defined as the DZ width. An alternative value can also be set from outside if desired.

Next, the method (2) of measuring the defect density per unit volume with respect to the depth from the surface of the specimen by image-processing on the basis of the scattered image will be explained.

Steps S1~S3 and S5~S7 in FIG. 11 represent the procedures of this method (2). Since Steps S1~S3 are the same as those of the method (1) described above, their explanation will be omitted.

After the scattered image is obtained by Steps S1~S3, binary-coding processing is carried out in Step S5. This processing is as follows. The scattered image obtained in Steps S1~S3 is, for example, the one shown in FIG. 12(a). Various defects 121 having different scattered light intensity exist in this scattered image. A binary image in which the regions having defects are represented by "1" and those having no defect are represented by "0" is obtained from this scattered image in accordance with the existence and absence of the defect while neglecting the differences in the scattered light intensities. FIG. 12(b) shows such a binary image. Reference numeral 122 represents the defect portions after binary-coding processing. The existence and absence of the defects in this binary-coding processing is judged using a predetermined scattered light intensity value as a threshold level and this predetermined scattered light intensity value is preferably one with respect to which the noise of the TV camera can be eleminated and at which the defect density to be measured in a later-appearing FIG. 12(c) becomes maximal.

After binary-coding processing, shrinking processing is conducted, Step S6. This shrinking processing is the one that separates, one by one, the defects represented by binary-coding and shrinks each defect to one point. The shrinking processing includes simply-connected shrinking in which a processing of converting an erasable 1-pixel (a pixel having a value "1") to "0" to the image and multiply-connected shrinking in which even a multiply-connected component can be shrunk, too, to one point (see "Introduction of Computer Image Processing", published by Soken Shuppan, Page 80.). FIG. 12(c) shows the image after such shrinking processing. Reference numeral 123 represents the defect portions subjected to shrinking processing.

Next, the defect density distribution and the DZ width are obtained in Step S7. In FIG. 12(c), a window 124 for counting the defect density, which is narrower than the DZ width, is set as shown in FIG. 12(c). The number of defects is counted by moving this window 124 as indicated by arrow 125. A distribution diagram of the defect density from the surface to the back of the specimen 111 is obtained. (see the graph 118 of FIG. 10) The DZ width is determined as the distance from the surface to the position at which the defect density reaches a predetermined value. In this embodiment, the DZ width is from the surface of the specimen 111 to the position inside the specimen at which the scattered light intensity reaches 30% of the maximum value of the scattered light intensity. The DZ width can be set separately from outside to a suitable value besides the value described above.

If a plurality of kinds of defects exist, they are distinguished by changing the threshold level in the binary-coding processing described above or by effecting shape recognition of the defects (see "Introduction of Computer Image Processing" described above, page 85, etc) and the density distribution as well as the DZ width can be measured in accordance with each kind of defect.

Figure 13:
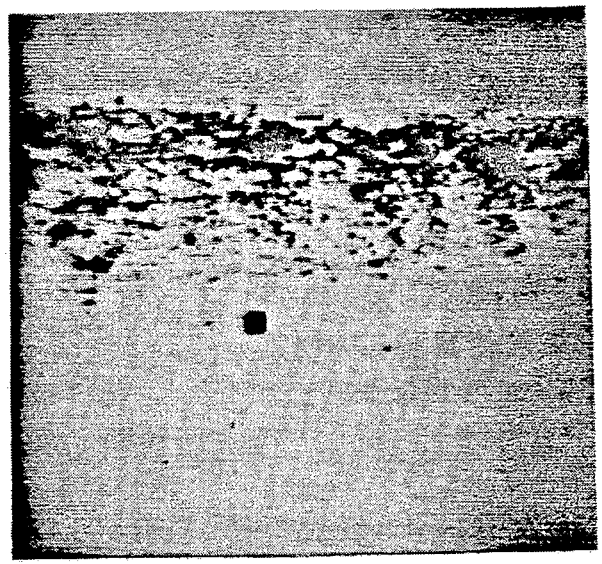
FIG. 13 is a photograph showing a crystal defect structure taken by using the apparatus shown in FIG. 9.

FIG. 13 is a photograph obtained by imaging the section of the crystal displayed on CRT by use of the apparatus shown in FIG. 9. The specimen is a GaAs crystal. The black portions represent the defect portions. (A black square portion near the center is a pointer displayed on the screen but is not a defect.) Such an image can be obtained in Step S3 in FIG. 11. The defect intensity inside the specimen and the DZ width can be measured from this image data in Steps S5~S7 described above.

Figure 14:
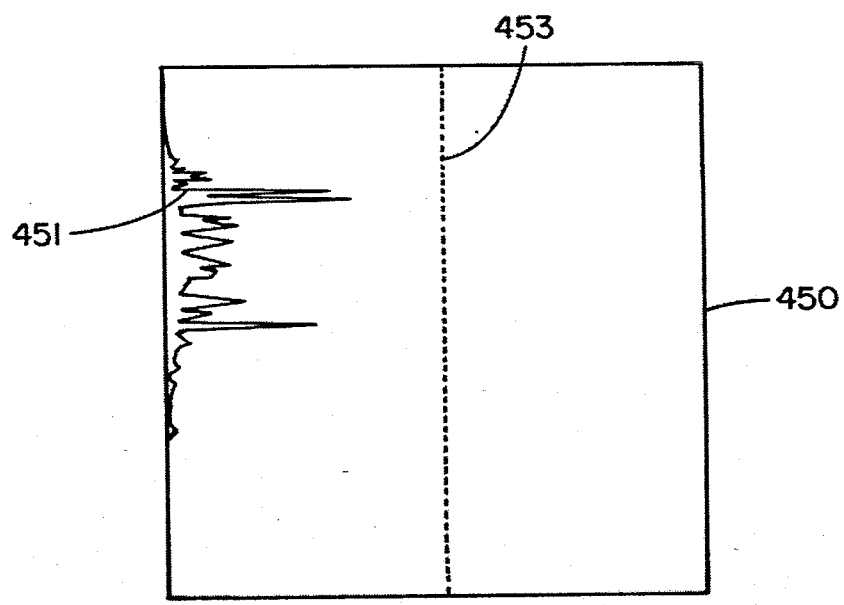
FIG. 14 is a diagram showing the scattered light intensity with respect to each position in the vertical direction.

FIG. 14 is a diagram showing the scattered light intensity with respect to each position in the vertical direction. A square frame 450 represents the section of the specimen corresponding to the photograph of FIG. 13. The graph 451 represents the scattered light intensity along a line 453 of this section (corresponding to the line in the vertical direction at the center of the photograph of FIG. 13). The graph 451 corresponds to the unidimensional distribution of the scattered light intensity obtained in Step S4 of FIG. 11 described above. The DZ width can be measured in Step S4 on the basis of this graph 451.

Figure 15:
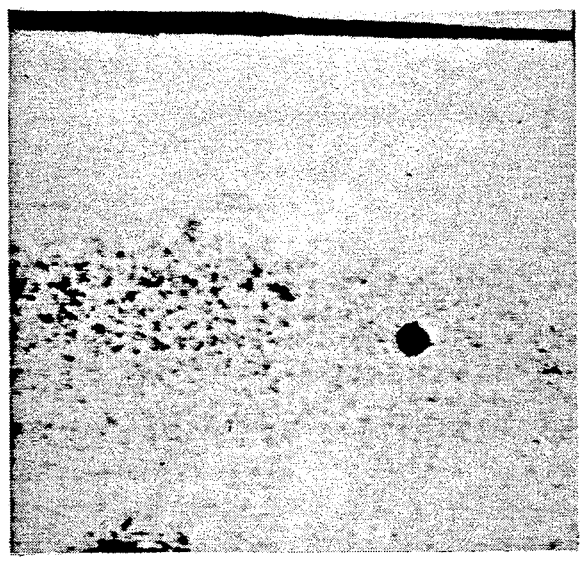
FIG. 15 is a photograph showing a crystal defect structure taken by using the apparatus of FIG. 9.
Figure 16:
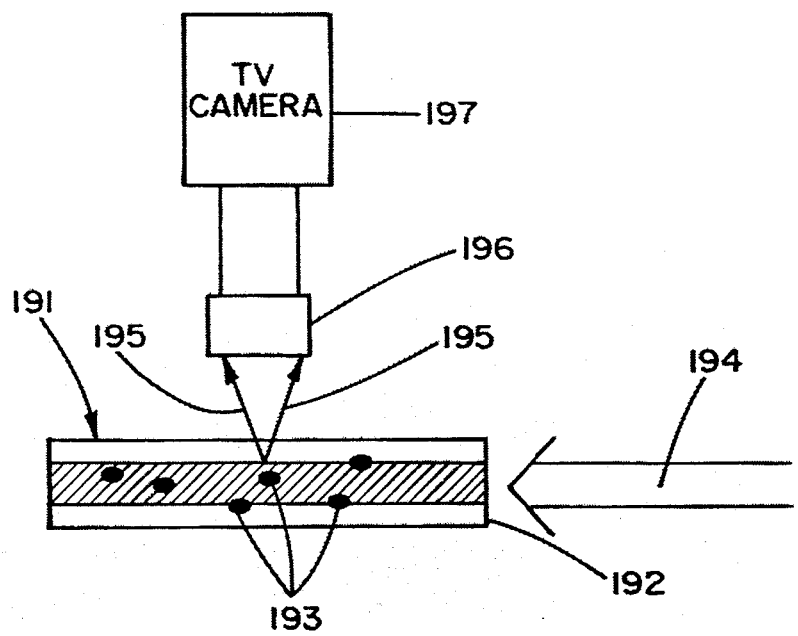
FIG. 16 is a block diagram showing a schematic structure of a conventional internal defect measuring apparatus.

FIG. 15 is another photograph obtained by imaging the section of the Si crystal displayed on CRT by use of the apparatus of FIG. 9 described before. The defects are black portions in the photograph.

In the embodiment described above, the case where the data of the two-dimensional internal defects in the vertical section of the specimen are measured was explained, but data of an arbitrary section can be obtained besides the section described above. For instance, defect data can be obtained about a horizontal section at a predetermined depth from the surface of the specimen. The defect data can be obtained about the section in an arbitrarily diagonal direction by controlling the movement of the pulse stage 912 in FIG. 9 using a computer. Furthermore, three-dimensional data of internal defects can be obtained by repeating the measurement in the vertical section while gradually moving the specimen in the X-axis direction in the apparatus shown in FIG. 9.

Examples of the wavelength tunable laser in the embodiment described above include a solid-stage wavelength tunable laser such as a titanium-sapphire laser and a dye laser, but any wavelength tunable laser can be used.

In the embodiment described above, the optical image obtained by the microscope is converted to the electric signal by use of the TV camera but other imaging devices, or light reception devices, may be used in place of the TV camera. The device for converting the optical image to the electric signal need not be two-dimensional one. Therefore, a unidimensional line sensor or a O-dimensional light receiving device can be used.

The specimens to be inspected in the present invention are single crystals of various oxides, single crystals of semiconductors and glass such as optical fibers. The specimen may be any object which permits the passage of a predetermined quantity of laser light.

In accordance with the present invention as described above, the finely contracted laser beam is allowed to be incident into the specimen from its surface and the scattered light from inside the specimen of the laser beam are observed on the surface side of the specimen and from a direction different to the optical axis of the incident laser beam. Accordingly, the internal defects can be detected and measured from an arbitrary position without destroying the specimen.

A scattered beam having low intensity can be detected, too, by ensuring that the observation path of the scattered light from inside the specimen, and the surface reflectance of the laser beam do not coincide.

If the wavelength of the laser beam or the temperature of the specimen is changed, the depth of incidence of the laser beam from the surface of the specimen can be changed. In this manner, the beam which is introduced into the specimen from the surface is reflected from the back surface, however, such a noise can be attenuated and scattered light from defects having a lower intensity can be detected. Particularly when the specimen is a semiconductor material such as silicon (Si) or gallium arsenide (GaAs), the depth of incidence of the laser beam from the surface can be easily adjusted of suitable wavelength corresponding to the energy gap of the semiconductor material as the specimen.

The image of the section scanned by the laser beam can be obtained easily by causing the laser beam to scan inside the specimen.

What is claimed is:

1. A methd of measuring internal defects of a specimen having a flat surface through which the defects are to be measured and which is sufficiently smooth for a laser beam to be incident into the specimen, comprising the steps of:
    allowing a laser beam to be incident into the specimen through said flat surface; and
    observing the scattered light of the incident laser beam from the defects through said flat surface and in a direction different from the optical axis of the incident laser beam,
    wherein the laser beam is finely contracted whereby the observed position of each defect corresponds to the depth of the defect.

2. The method according to claim 1, wherein said scattered light is observed from a direction in which the reflected part of the incident beam from said flat surface is not incident.

3. The method according to claim 1, which further comprises a step of tuning the wavelength of the laser beam so as to obtain a desired depth of incidence of the laser beam from said flat surface.

4. The method according to claim 1, which further comprises a step of changing the temperature of the specimen to change the depth of incidence of the laser beam from said flat surface.

5. The method according to claim 1, which further comprises a step of effecting relative movement between the laser beam and the specimen so that finely contracted beam moves along a section, thereby scanning the specimen along the section with the laser beam and observing a two-dimensional image of the defects on the section.

6. An apparatus for measuring internal defects of a specimen having a flat surface through which the defects are to be measured and which is smooth enough for a laser beam to be incident into the specimen, comprising:
    means for allowing a laser beam to be incident into the specimen through said flat surface; and
    means for observing the scattered light of the incident laser beam from the defects through said flat surface and in a different direction from the optical axis of the incident laser beam,
    wherein the laser beam is finely contracted and the observed position of each defect corresponds to the depth of the defect.

7. The apparatus according to claim 6, wherein said scattered light is observed by said observation means from a direction in which the reflected part of the incident beam from said flat surface is not incident.

8. The apparatus according to claim 6, which further comprises means for tuning the wavelength of the laser beam so as to obtain a desired depth of incidence of the laser beam from said flat surface.

9. The apparatus according to claim 6, which further comprises means for changing the temperature of the specimen to change the depth of incidence of the laser beam from said flat surface.

10. The apparatus according to claim 6, which further comprises means for effecting relative movement between the laser beam and the specimen thereby scanning the specimen along the section with the laser beam and observing a two-dimensional image of the defects on the section.

11. The method according to claim 5, which further comprises a step of effecting relative movement between the laser beam and the specimen in a direction intersecting the said section, thereby observing a three-dimensional image of the defects existing in the scanned portion.

12. The method according to claim 3, wherein the material of the specimen is a semiconductor, and the wavelength of the laser beam is within the range corresponding to the energy gap of the semiconductor.

13. The method according to claim 4, wherein the material of the specimen is a semiconductor, and the wavelength of the laser beam is within the range corresponding to the energy gap of the semiconductor.

14. The apparatus according to claim 10, which further comprises means for effecting relative movement between the laser beam and the specimen in a direction intersecting at least part of said light beam, thereby observing a three-dimensional image of the defects existing in the scanned portion.

15. The apparatus according to claim 8, wherein the material of the specimen is a semiconductor, and the wavelength of the laser beam is within the range corresponding to the energy gap of the semiconductor.

16. The apparatus according to claim 9, wherein the material of the specimen is a semiconductor, and the wavelength of the laser beam is within the range corresponding to the energy gap of the semiconductor.

* * * * *